US009511256B2

(12) United States Patent
Barriskill et al.

(10) Patent No.: US 9,511,256 B2
(45) Date of Patent: Dec. 6, 2016

(54) SUPINE CYCLE

(71) Applicants: Andrew Bruce Barriskill, Baltimore, MD (US); Scott Simcox, Baltimore, MD (US); Robert Flesher, Baltimore, MD (US); Susan Harkema, Louisville, KY (US)

(72) Inventors: Andrew Bruce Barriskill, Baltimore, MD (US); Scott Simcox, Baltimore, MD (US); Robert Flesher, Baltimore, MD (US); Susan Harkema, Louisville, KY (US)

(73) Assignee: RESTORATIVE THERAPIES, INC., Baltimore, MD (US)

( * ) Notice: Subject to any disclaimer, the term of this patent is extended or adjusted under 35 U.S.C. 154(b) by 0 days.

(21) Appl. No.: 14/713,915

(22) Filed: May 15, 2015

(65) Prior Publication Data

US 2016/0016036 A1    Jan. 21, 2016

Related U.S. Application Data

(60) Provisional application No. 61/994,957, filed on May 18, 2014.

(51) Int. Cl.
| | |
|---|---|
| *A63B 24/00* | (2006.01) |
| *A63B 22/06* | (2006.01) |
| *A61H 1/02* | (2006.01) |
| *A63B 21/005* | (2006.01) |
| *A63B 22/00* | (2006.01) |
| *A63B 21/00* | (2006.01) |
| *A61N 1/36* | (2006.01) |
| *A63B 23/035* | (2006.01) |
| *A63B 71/02* | (2006.01) |

(52) U.S. Cl.
CPC ......... *A63B 22/0605* (2013.01); *A61H 1/0214* (2013.01); *A61H 1/0237* (2013.01); *A61H 1/0274* (2013.01); *A61N 1/36003* (2013.01); *A61N 1/36014* (2013.01); *A63B 21/0058* (2013.01); *A63B 21/00178* (2013.01); *A63B 21/00181* (2013.01); *A63B 21/1672* (2015.10); *A63B 22/0005* (2015.10); *A63B 22/0007* (2013.01); *A63B 22/0694* (2013.01); *A63B 24/0087* (2013.01); *A61H 2201/0142* (2013.01); *A61H 2201/0157* (2013.01); *A61H 2201/10* (2013.01); *A61H 2201/1215* (2013.01); *A61H 2201/1638* (2013.01); *A61H 2201/1642* (2013.01); *A61H 2203/0437* (2013.01); *A63B 21/4019* (2015.10); *A63B 21/4021* (2015.10); *A63B 23/03508* (2013.01); *A63B 2022/0038* (2013.01); *A63B 2022/0617* (2013.01); *A63B 2022/0652* (2013.01); *A63B 2071/025* (2013.01); *A63B 2208/0238* (2013.01); *A63B 2213/004* (2013.01)

(58) Field of Classification Search
CPC .............. A63B 24/00; A63B 24/0087; A63B 22/0694; A63B 22/0605; A63B 22/007; A63B 22/005; A63B 21/0058; A63B 21/00178; A63B 21/00181; A63B 21/4019; A63B 21/4021; A63B 21/1672; A63B 22/0007; A61H 1/0281; A61H 1/0259; A61H 3/04; A61H 1/0214; A61H 1/0237; A61H 1/0274; A61H 2201/0142; A61H 2201/10; A61H 2201/1215; A61H 2201/1638; A61H 2201/1642
See application file for complete search history.

(56) References Cited

U.S. PATENT DOCUMENTS

| | | | | | |
|---|---|---|---|---|---|
| 3,488,088 | A | * | 1/1970 | Goldberg | ................. A61H 3/04 297/5 |
| 4,601,464 | A | * | 7/1986 | Mousel | .............. A63B 22/0694 482/60 |
| 6,152,855 | A | * | 11/2000 | Dean, Jr. | ............... A61H 1/0259 482/114 |
| 6,695,795 | B2 | * | 2/2004 | Knoll | .................... A61H 1/0281 601/26 |
| 2015/0190667 | A1 | * | 7/2015 | Balandis | ............ A63B 24/0087 482/5 |

* cited by examiner

*Primary Examiner* — Glenn Richman
(74) *Attorney, Agent, or Firm* — Whiteford, Taylor & Preston, LLP; Peter J. Davis

(57) ABSTRACT

A therapeutic muscle exercise device for assisting subjects in maintaining and regaining muscle tone through the use of functional electrical stimulation has an extremity support and a functional electrical stimulation controller. The extremity support is mounted on a mobile support which allows the device to be easily used when the subject is laying on a bed.

10 Claims, 8 Drawing Sheets

SUPINE CYCLE

CROSS-REFERENCE TO RELATED APPLICATIONS

This application claims priority from U.S. Provisional Application Ser. No. 61/994,957 filed on May 18, 2014, with the United States Patent and Trademark Office and entitled SUPINE CYCLE. The application is incorporated herein by reference in its entirety.

BACKGROUND

1. Field of the Invention

This invention relates to a training device for rehabilitation of individuals confined to a bed. More particularly, the present invention relates to a device to assist patients perform leg or arm exercises while lying on their back.

2. Description of the Background

Critical illness creates new physical, cognitive, and mental health impairments that compounds pre-existing dysfunction. Intensive care unit ICU-acquired weakness is one of the most important and common results of critical illness. More than 50% of ICU survivors suffer cognitive impairment, and 30% report anxiety and depression, or have persistent post-traumatic-stress disorder symptoms in the 2 years following their ICU discharge. Only 50% resume work by 1 year and 69% are still restricted in performing daily activities. These issues are collectively called "post-intensive care syndrome." They affect up to 70% of Intensive Care Unit (ICU) survivors, are often long-lasting. Acute ICU-based rehabilitation has been shown to be feasible, safe and to improve patient important outcomes.

There is a need for devices that assist patients who cannot stand or sit, such as patients in ICU, in conducting leg exercises to maintain or gain muscle tone and abilities. Patients typically need to be moved to utilize machines that provide exercise assistance. Such machines require either that the patient be moved in bed or even lifted from a hospital or patient bed onto the machine.

SUMMARY OF THE INVENTION

One object of the present invention is to provide an exercise device that allows a patient to maintain leg muscle tone and abilities without requiring repositioning of the patient in bed. As shown on the figures, one embodiment of the present invention provides an exercise machine that can slide above the surface of a patient's bed in order to allow the patient to conduct supine leg or arm cycle training. The machine does not require that the patient be moved onto a machine or repositioned in bed and, thus, makes it much easier to treat patients who require treatment without the risks and time involved with moving the patient.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION

Figure 1:
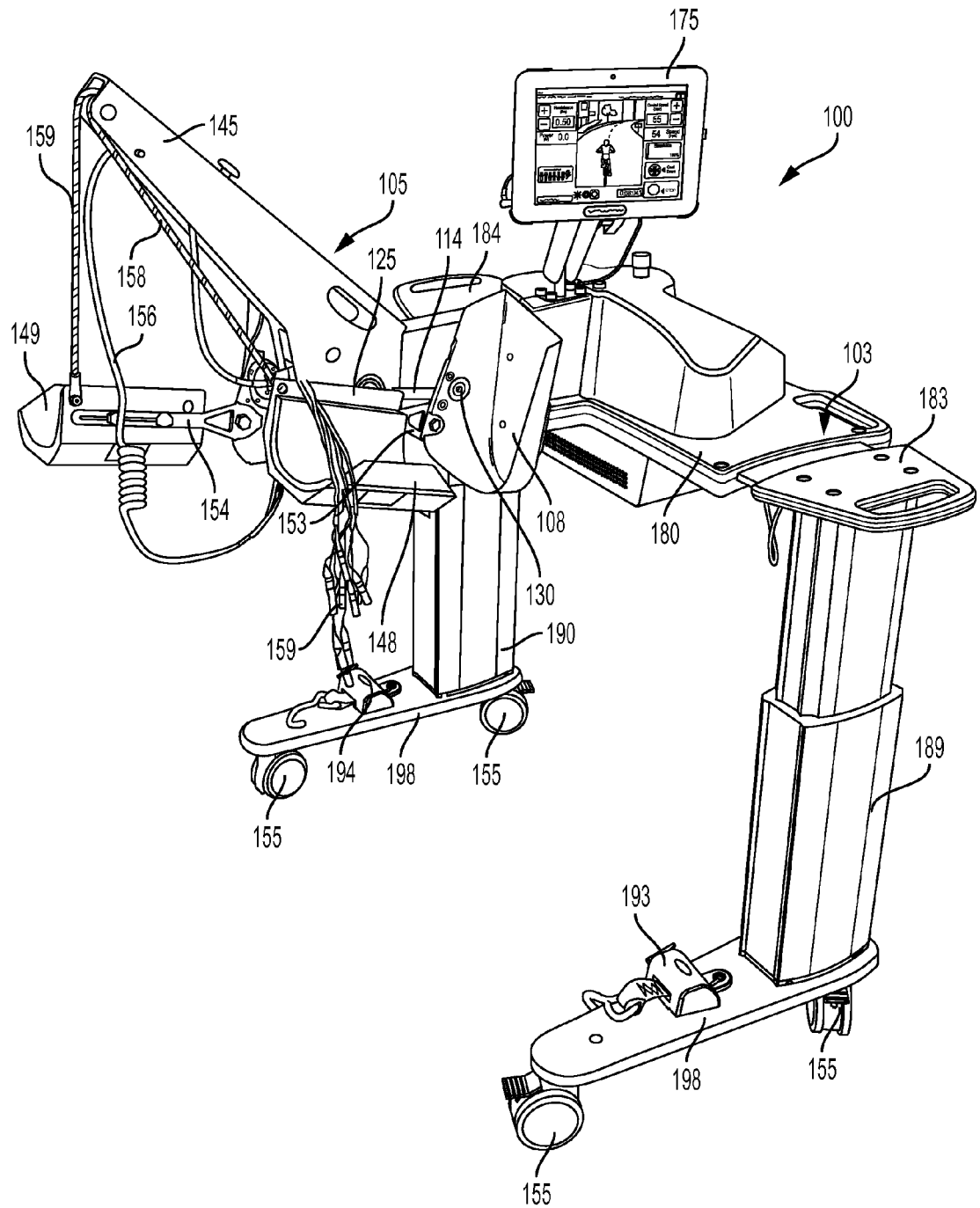
FIG. 1 is a perspective picture of a device in accordance with one embodiment of the invention.
Figure 2:
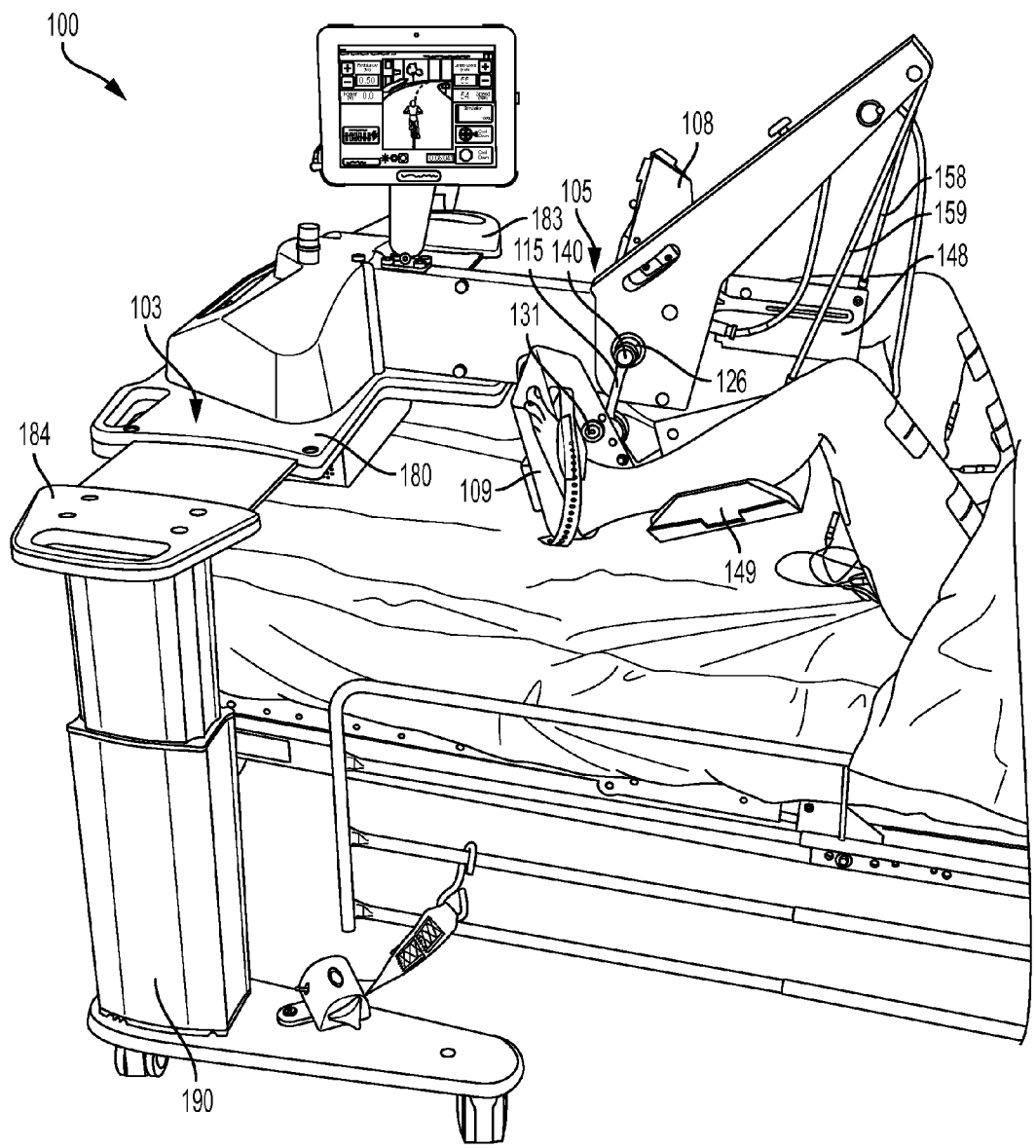
FIG. 2 is a picture of one embodiment of the present invention in use.
Figure 3:
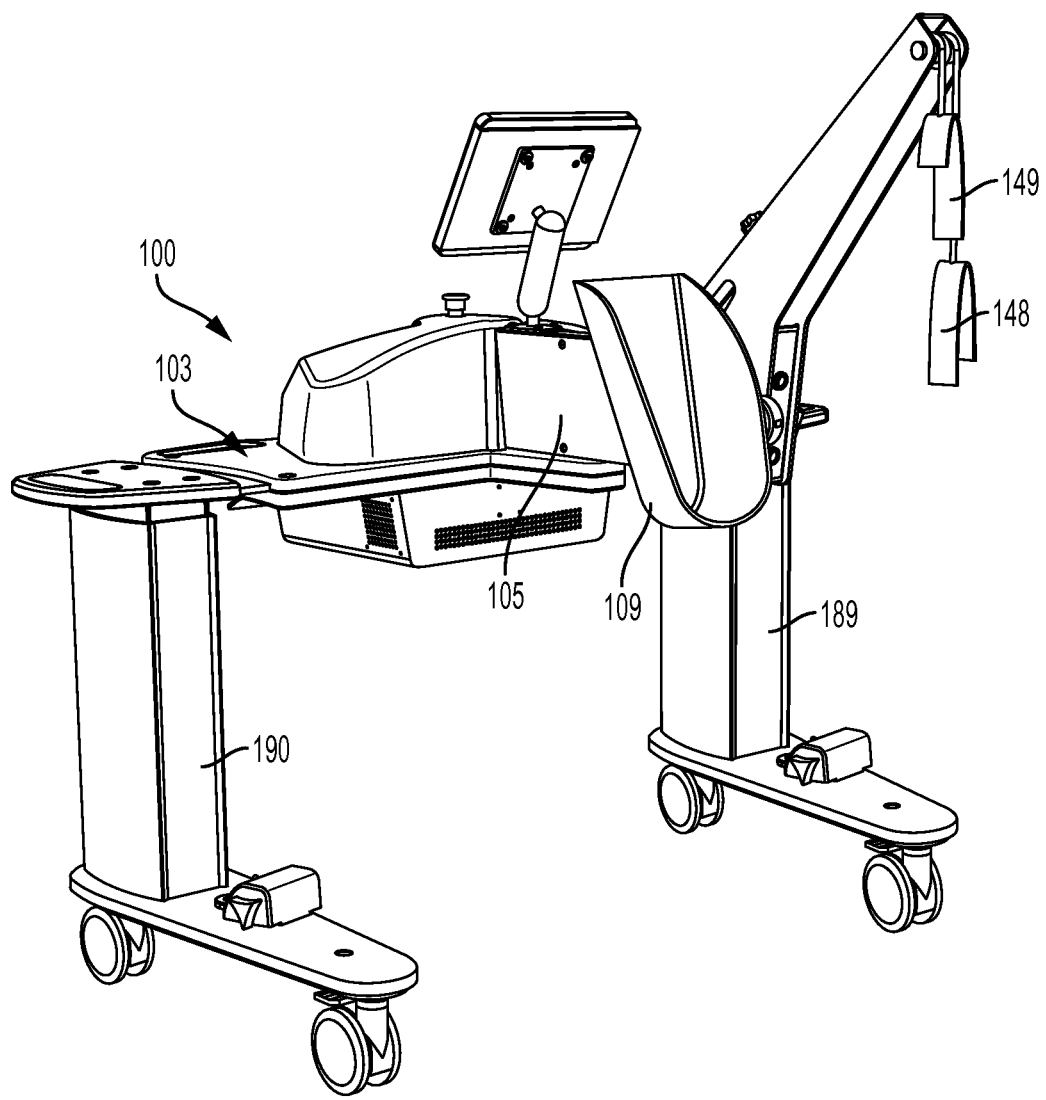
FIG. 3 is a perspective diagram of one embodiment of the present invention.
Figure 4:
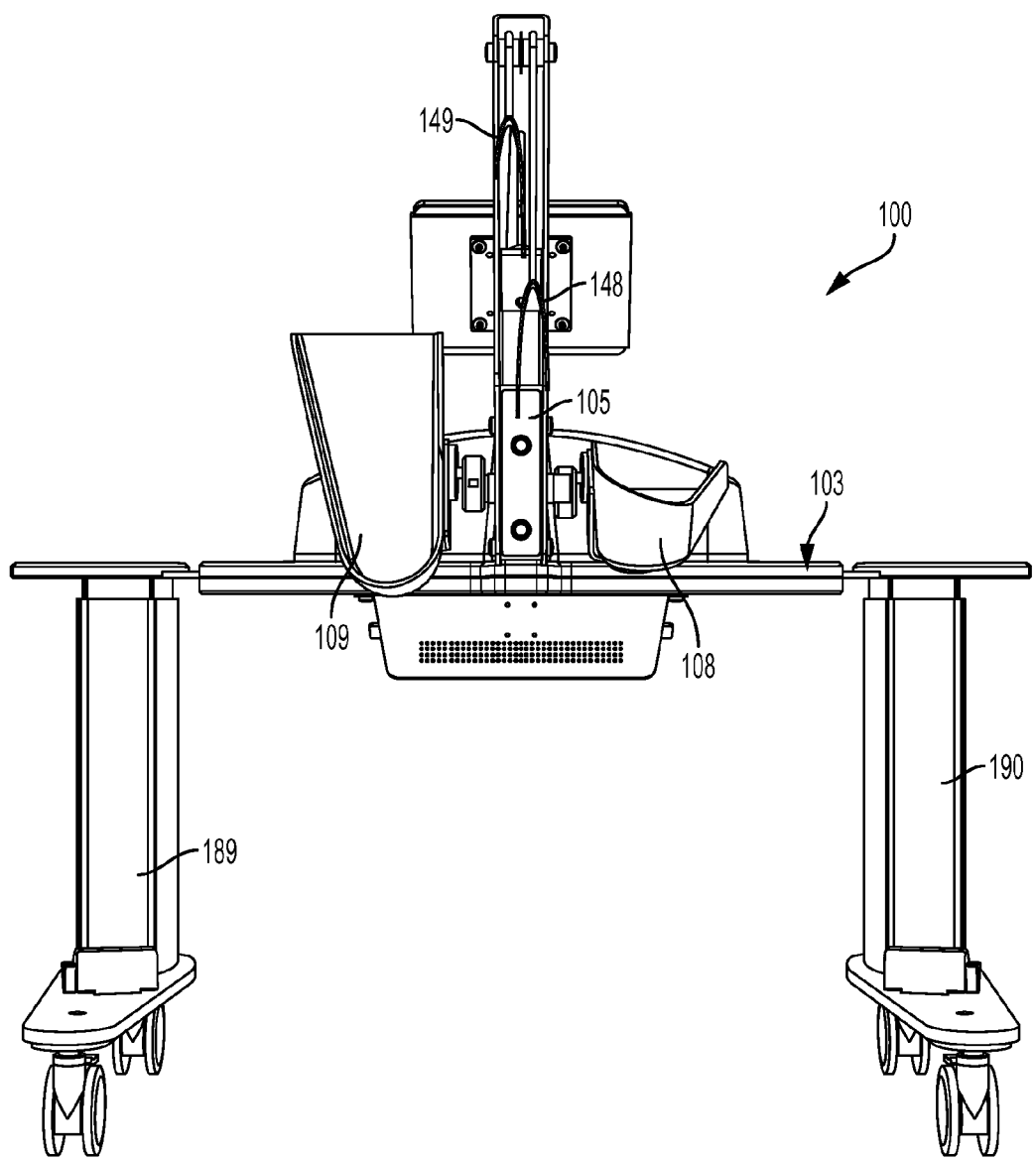
FIG. 4 is a front diagram of a device in accordance with one embodiment of the present invention.
Figure 5:
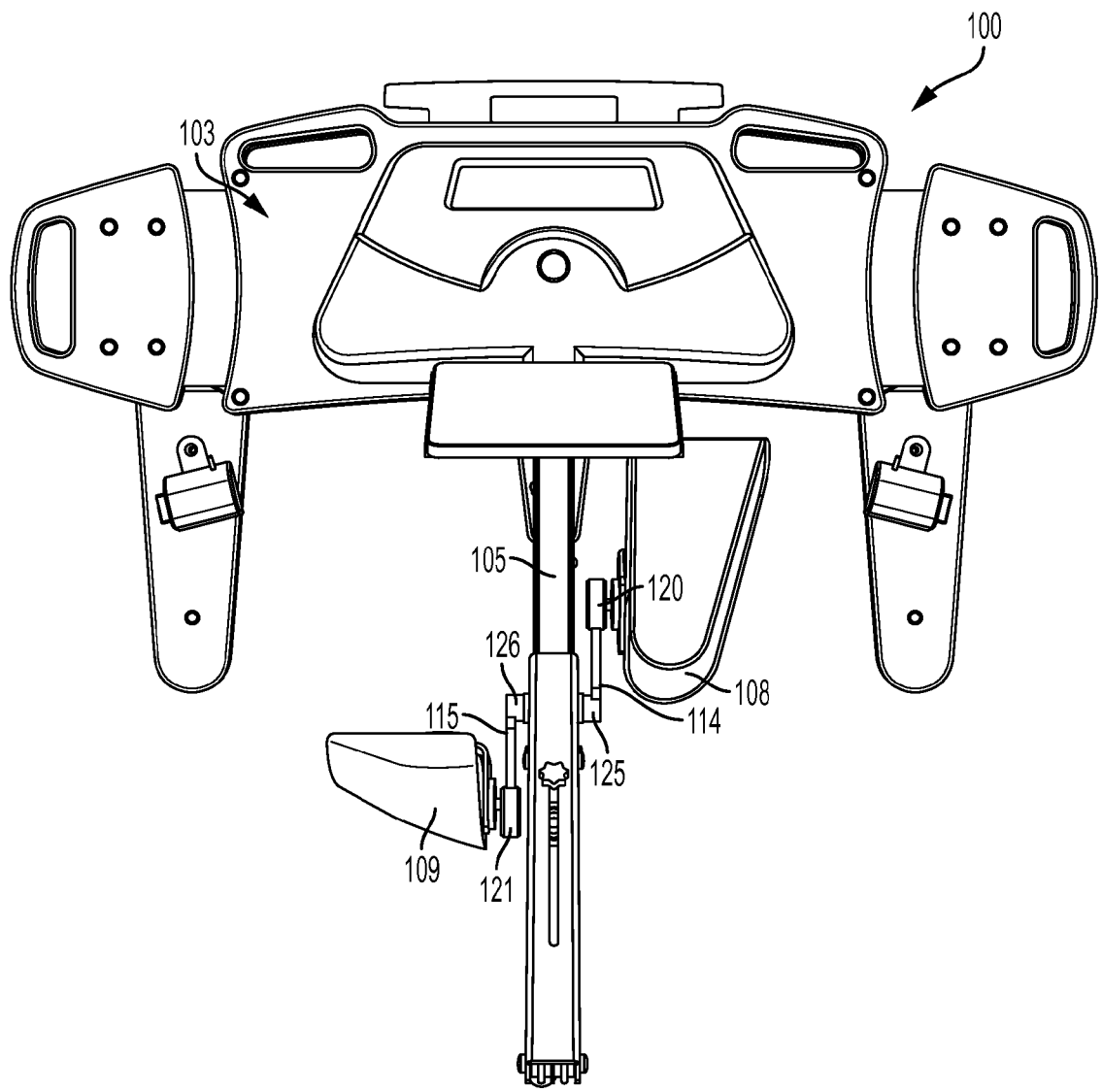
FIG. 5 is a top diagram of a device in accordance with one embodiment of the present invention.
Figure 6:
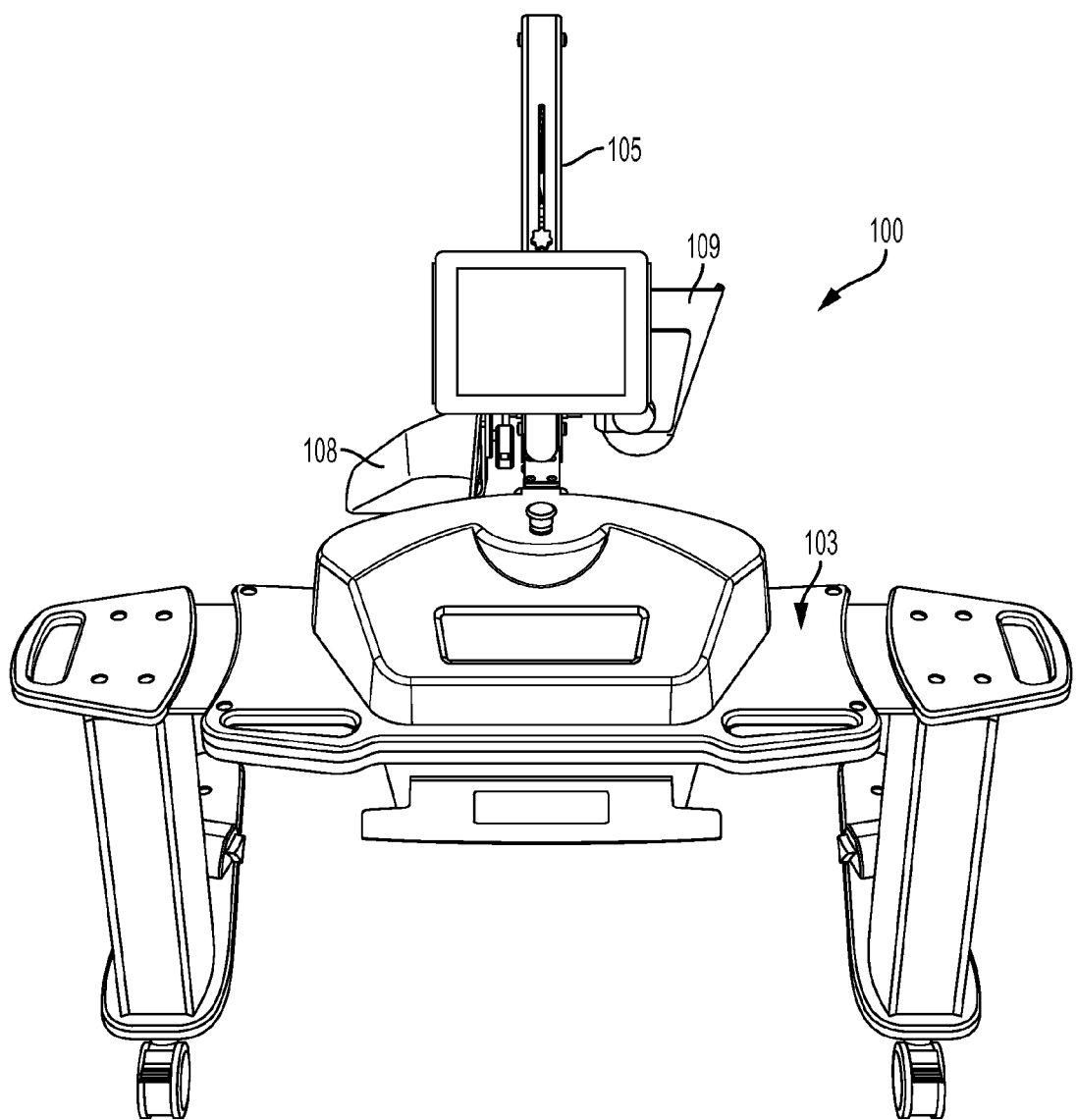
FIG. 6 is a rear diagram of a device in accordance with one embodiment of the present invention.
Figure 7:
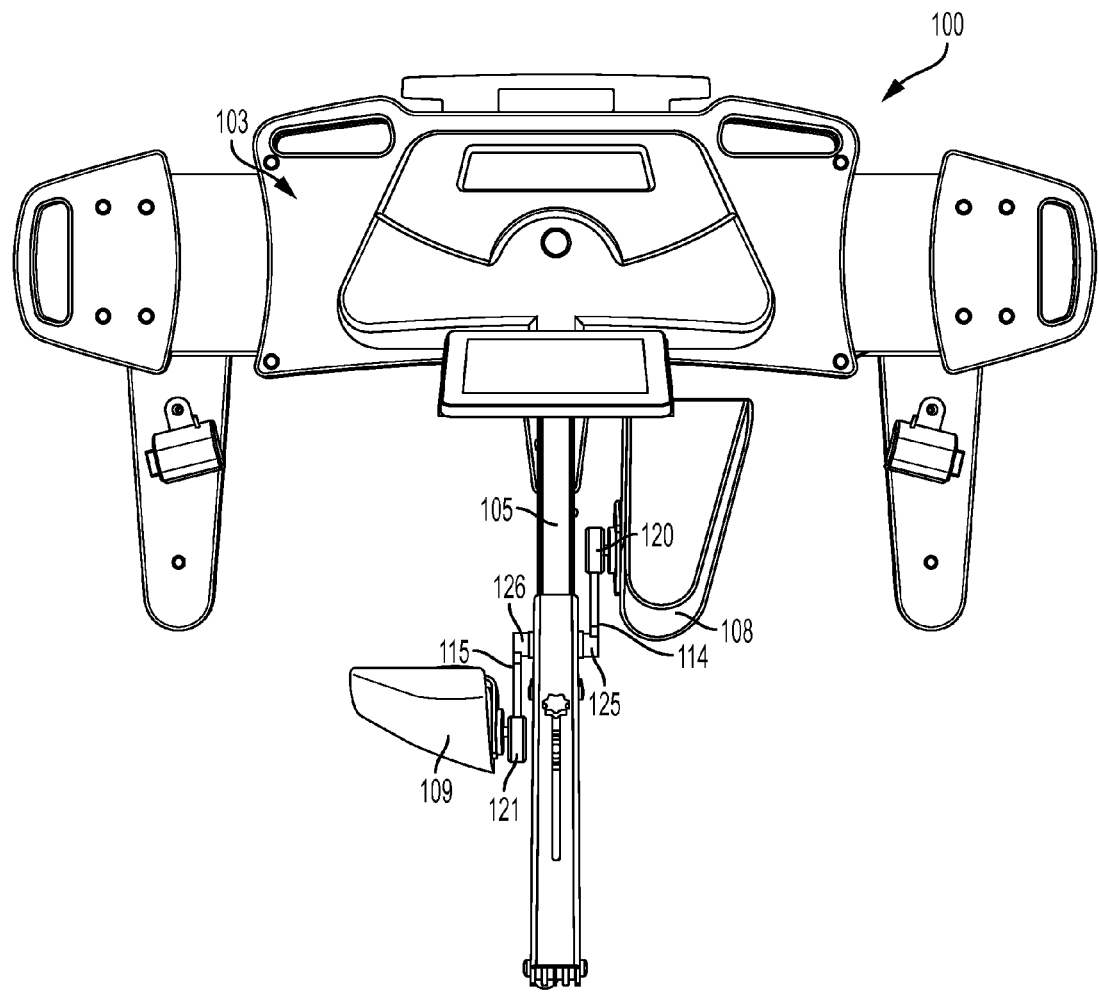
FIG. 7 is a top diagram of a device with extended sides in accordance with one embodiment of the present invention.

The invention summarized above may be better understood by referring to the following description, the accompanying drawings, and the claims listed below. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

As shown in FIGS. 1 through 7, one embodiment of the present invention comprises a therapeutic muscle exercise device 100, (also referred to herein as a supine cycle), used to treat patients who are not capable of walking, sitting, or standing. The supine cycle 100 comprises a cycling base 105 that is mounted on a mobile support 103. In some embodiments, the mobile support 103 is an expandable table (as explained in more detail below) that fits over a hospital bed, allowing the cycle to be brought to the patient.

The cycling base 105 has a first extremity support 108 and a second extremity support 109. It is contemplated that in some embodiments a single extremity support may be included to facilitate treatment of subjects who have lost a limb. Each extremity support 108 and 109 are attached to the cycling base by a first rotating arm 114 and a second rotating arm 115, respectively. Each rotating arm as a extremity support end 120, 121 and a base end 125, 126.

The rotating arms 114 and 115 attach to the extremity supports 108 and 109 at a extremity support pivot point 130 and 131. The configuration allows the foot of the subject to rotate as normally as it would when performing a cycling motion naturally. The base ends 125 and 126 connect to the cycling base 105 at a base pivot point 140. In a preferred embodiment, the base pivot point 140 comprises a shaft that passes through a channel that extends through the base; the shaft connects the base end 125 of the first rotating arm 114 to the base end 126 of the second rotating arm 115. In such embodiment, the shaft then rotates uniformly around the base pivot point 140. In other embodiments, the rotating arms 114, 115 may connect to two independently rotatable shafts at the base pivot point 140 allowing the extremity supports 108 and 109 to rotate independently of one-another.

The cycling base 105 also includes a support boom 145 that provides support for two calf supports 148, 149. In some embodiments, the calf supports 148 and 149 are connected to the extremity supports 108 and 109 though an attachment link 153, 154. In other embodiments, the calf supports 148 and 149 may not be linked to the extremity supports 108 and 109. The support boom 145, in some embodiments includes a set of pulleys that allow a support cord 158, 159 to provide support for the calf supports 148 and 149. In addition, the support boom 145 provides support for a lead cable 156 that encases the various leads 159 used to provide functional electrical stimulation (FES) to the subject's muscles.

The device 100 also includes a functional electrical stimulation controller 175. The controller 175 manages the electrical impulses provided to the subject's muscles through a series of leads 159, which are connected to the controller 175 through a lead cable 156. The controller 175 also controls a motor (not shown) that controls the speed of rotation of the rotating arms 114 and 115. The controller 175 coordinates the rotation of the rotating arms 114 and 115 in conjunction with functional electrical stimulation through the leads 159 depending on the level of need of the subject. In some instances, the controller 175 will direct full movement of the rotating arms 114 and 115 in conjunction with electrical stimulation resulting in fully FES evoked movement. In the alternative, the controller 175 may reduce the level of assistance provided by the motor and the electrical stimulation allowing volitional movement by the subject. In yet a further embodiment, the controller 175 will not provide any assistance in order to allow the subject to rotate the extremity supports 108, 109 without assistance. The controller 175 provides such assistance as needed by the subject and directed by the user.

In one preferred embodiment, the cycling base 105 is mounted on a mobile support 103. The purpose of the mobile support 103 is to allow a practitioner to slide the cycling base 105 above the bed where a subject is laying without having to remove the base and place it on the bed. Many different types of mobile support 103 combinations may be used. In one exemplary embodiment as shown here, mobile support 103 has a main base 180 and two horizontally extendible arms 183 and 184. The extendible arms 183 and 184 are attached to two rolling and telescoping legs 189,190. The dual telescoping legs 189, 190, provide significant stability to device 100.

The telescoping legs 189,190 in one preferred embodiment are placed on rolling boards 197, 198. For stability, the rolling boards 197, 198, may be placed on rolling wheels 155. As understood by a person of ordinary skill in the art, any types of wheels 155 may be used, including wheels that have breaking mechanisms to prevent the unit from moving once engaged. The mobile support 103 may also include latches 193,194 that allow the user to lock the unit in place and prevent it from sliding, even when the wheel brakes are engaged. One particular advantage of the supine cycle described herein is the capability to expand the table in order to avoid obstacles under the bed. As shown on the figures, the supine cycles is placed on a moveable base or table that can slide over the patient's bed. It is configured, however, so that it will have no protrusions under the bed that may interfere with the use of the supine cycle.

As described above, the controller is configured to optionally provide FES. FES relates to electrical stimulation applied to peripheral nerves to produce a function. Reversing muscle atrophy and bone loss are the primary clinical benefits of neuromuscular electrical stimulation. Increases in bone density are directly related to the level of torque generated by the muscle.

In one embodiment, a method for exercising a subject's lower extremities is provided. According to this embodiment, the system continuously rotates at the set speed and it either assists or resists the patient's efforts. The patient's efforts are either volitional or evoked by FES. In a first step of the method the system's motor moves the subject's lower extremities and the controller provides initial muscle electrical stimulation. This first step can be referred to as a warm up step. In a subsequent step, referred to as active transition, the controller increases muscle electrical stimulation and reduces motor assistance until the muscle takes over movement of the extremity supports or 100% stimulation threshold is reached. In a subsequent step, referred to as the active step, electrical stimulation evokes coordinated muscle contractions as the rotating arms 114 and 115 turn around the pivot point 140 resulting in the subject's muscles performing the cycling motion. The combination of the rotating arms 114 and 115 connected at the pivot point 140 is also referred to herein as the crank. Once muscle fatigue is reached and/or detected by the controller, electrical stimulation is reduced and the motor of the cycling base takes over for cycling motion. In a final step, referred to as cool down, the motor completely takes over cycling motion allowing subject's muscles to rest while permitting movement through the range of motion.

In another embodiment, the cycle crank moves to set positions to position the muscles for isometric contractions which are FES evoked. The approximate length for optimal contraction is determined for each muscle. The length-tension curve determines the force generated by the muscle at a given electrical activation. A muscle should be at the peak of the length tension curve in order to gain the optimal increase in muscle mass. In addition, an isometric contraction generates a greater force per a given activation of the muscle by electrical stimulation because of the resistance to the contraction provided. For optimal clinical benefit, the cycle is positioned at the coordinates that places each muscle group at their optimal muscle length and stops so an isometric contraction occurs. For each individual the coordinates are determined based on extensors and flexors of each joint for each joint. Muscles are stimulated when the crank reaches the coordinates relative the joint position. Multiple muscles of the right and left leg are stimulated simultaneously as appropriate.

|  | Hip | Knee | Ankle |
| --- | --- | --- | --- |
| Soleus | n/a | n/a | 90 degrees |
| Gastrocnemius | n/a | 45 degrees | 90 degrees |
| Tibialis Anterior | n/a | n/a | 45 degrees |
| Medial Hamstrings | 45 degrees | 60 degrees | n/a |
| Quadriceps | n/a | 60 degrees | n/a |
| Gluteals | 45 degrees | n/a | n/a |

Figure 8:
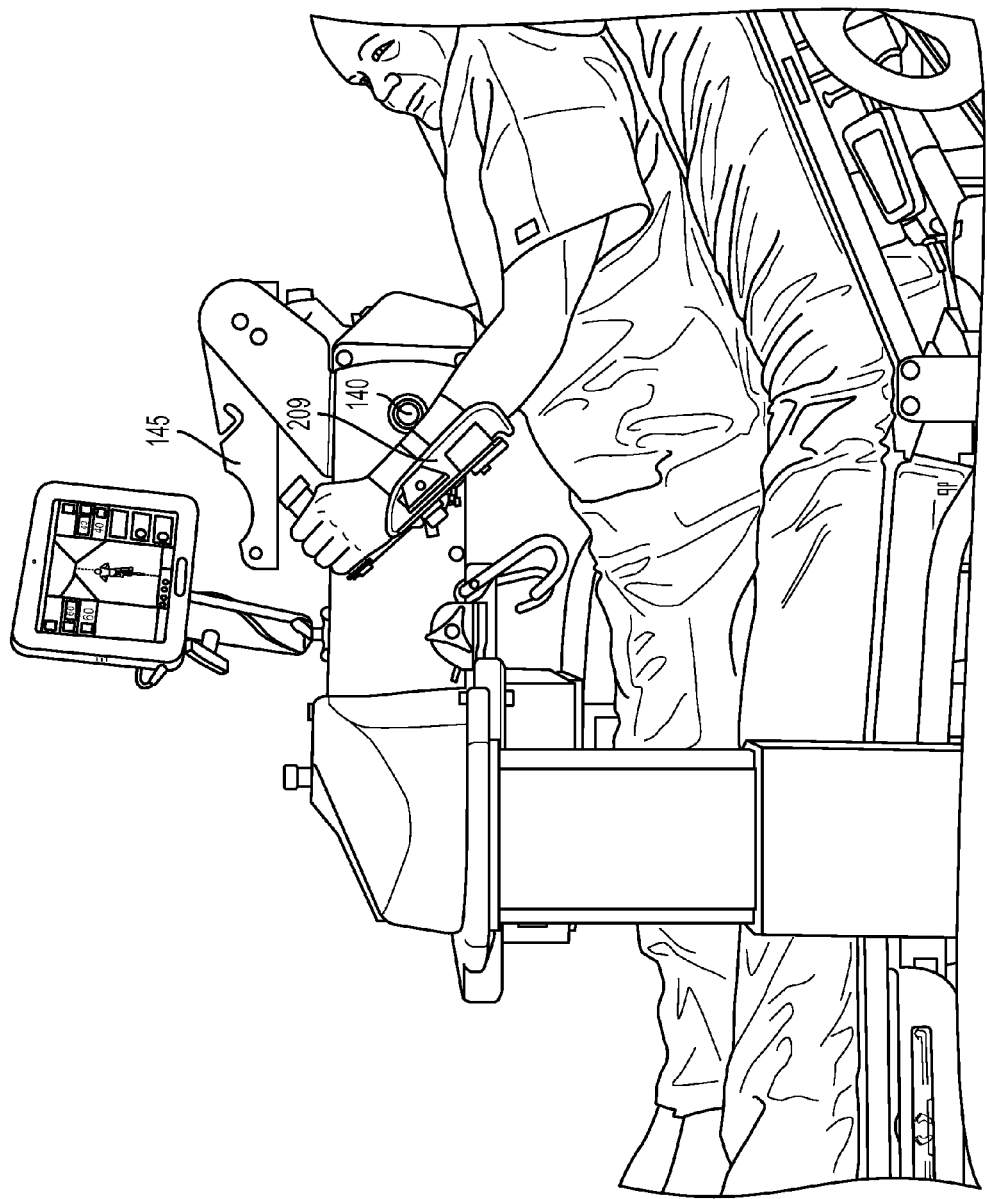
FIG. 8 is a side view of another embodiment of the invention.

According to a different embodiment, a device and method for exercising a subject's upper extremities is provided. Referring to FIG. 8, the present embodiment may have an overall configuration similar to the lower extremity embodiment described with reference to FIGS. 1-7, but wrist and hand supports 208 and 209 may be provided in place of extremity supports 108 and 109. According to a preferred embodiment, wrist and hand supports may be configured to attach to rotating arms 114 and 115 in place of extremity supports 108 and 109. Alternatively, a shorter or longer set of rotating arms 214 and 215 may be substituted for rotating arms 114 and 115 at base pivot point 140, and subsequent attachment to wrist and hand supports 208 and 209. According to this upper extremity embodiment, boom 145 may be rotated out of the way as shown in FIG. 8.

According to the method of this embodiment, in a first step of the method the system's motor moves the subject's upper extremities and the controller provides initial muscle electrical stimulation. This first step can be referred to as a warm up step. In a subsequent step, referred to as active transition, the controller increases muscle stimulation and reduces motor assistance until the muscle takes over movement of the arm supports or 100% stimulation threshold is reached. In a subsequent step, referred to as the active step, electrical stimulation evokes coordinated muscle contractions as the crank rotates resulting in the subject's muscles performing the arm cycling motion. Once muscle fatigue is reached and/or detected by the controller, electrical stimulation is reduced and the motor of the cycling base takes over for cycling motion. In a final step, referred to as cool down, the motor completely takes over cycling motion allowing subject's muscles to rest while permitting movement through the range of motion. In this embodiment the patient can we supine with different angles of back support, for example the patient could be arm cycling while fully supine, propped up at a 45 degree angle or fully seated at close to a 90 degree angle. In order for the electrical stimulation to be correctly coordinated with the crank rotation and position of the arms it is essential that the electrical stimulation control algorithm, make allowance for the seating angle. This is done by rotating the position of top dead center for the stimulation counter clockwise with respect to the position of mechanical top dead center. As an example, if the patient is lying in bed with their back propped up to a 45 degree angle the position of electrical top dead center will be rotated counter clockwise by 45 degrees with respect to mechanical top dead center.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A therapeutic muscle exercise device, comprising:
   a cycling base configured to accept a subject's upper or lower extremities and assist a subject in exercising the subject's muscles;
   a mobile support on which the cycling base is mounted and which that allows the cycling base to wheel over a subject's bed;
   first and second rolling and telescoping legs,
   and first and second horizontally extendible arms orthogonally attached to said first and second rolling and telescoping legs, respectively;
   said first and second horizontally extendible arms attached to and supporting opposite ends of said mobile support;
   wherein no portion of the device is configured to extend under the subject's bed.

2. The device of claim 1, wherein the cycling base comprises a first extremity support and a second extremity support and wherein said extremity supports are driven or resisted by a motor controlled by the controller.

3. The device of claim 2, further comprising a functional electrical stimulation controller, wherein the functional stimulation controller and the first and second extremity supports and cycling base are configured to assist a subject in moving his or her upper or lower extremities.

4. The device of claim 3, wherein the controller manages isometric functional electrical stimulation to the subject's muscles.

5. A method of exercising a subject's extremities while the subject is in bed, comprising:
   placing the subject's extremities in an extremity support of a device of claim 3;
   placing on the subject's extremities, and
   exercising the subject's extremities.

6. The method of claim 5, wherein said exercising step comprises actively assisting the subject in moving the subject's extremities by rotating the extremity supports around an extremity support pivot point.

7. The method of claim 6, further comprising assisting the subject to exercise the subject's extremities through isometric functional electrical stimulation.

8. The method of claim 7, further comprising increasing muscle electrical stimulation and reducing motor assistance.

9. The method of claim 8, wherein electrical stimulation evokes coordinated muscle contractions and the extremity supports' does not drive rotation.

10. The method of claim 9, further comprising increasing motor assistance and decreasing electrical stimulation.

* * * * *